US011040049B2

(12) United States Patent
McConnell et al.

(10) Patent No.: US 11,040,049 B2
(45) Date of Patent: *Jun. 22, 2021

(54) COMPOSITION COMPRISING HMSS/HMOS AND USE THEREOF

(71) Applicant: Glycom A/S, Hørsholm (DK)

(72) Inventors: Bruce McConnell, La Tour de Peilz (CH); Emma Elison, Hjärup (SE); Louise Kristine Vigsnæs, København NV (DK)

(73) Assignee: Glycom A/S, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/903,959

(22) Filed: Feb. 23, 2018

(65) Prior Publication Data
US 2018/0177809 A1    Jun. 28, 2018

Related U.S. Application Data

(63) Continuation-in-part of application No. 15/147,112, filed on May 5, 2016, now abandoned, which is a continuation-in-part of application No. 15/034,593, filed as application No. PCT/DK2015/050332 on Oct. 29, 2015, now abandoned.

(30) Foreign Application Priority Data

Oct. 29, 2014    (DK) ............... PA 2014 70663

(51) Int. Cl.
A61K 31/702    (2006.01)
A61K 31/7016   (2006.01)
A61P 1/12      (2006.01)

(52) U.S. Cl.
CPC ........ A61K 31/702 (2013.01); A61K 31/7016 (2013.01); A61P 1/12 (2018.01); A61K 2300/00 (2013.01)

(58) Field of Classification Search
CPC ............. A61K 31/703; A61K 31/7004; A61K 31/7016; A61K 2300/00
USPC ...................................................... 514/23
See application file for complete search history.

(56) References Cited

U.S. PATENT DOCUMENTS

| 4,663,321 | A | 5/1987 | Bock et al. | |
|---|---|---|---|---|
| 2007/0185094 | A1 | 8/2007 | Lattmann et al. | |
| 2012/0171165 | A1* | 7/2012 | Buck | A61K 31/702 514/23 |
| 2012/0171166 | A1 | 7/2012 | Chow et al. | |
| 2012/0172319 | A1 | 7/2012 | Chow et al. | |
| 2013/0195803 | A1 | 8/2013 | German et al. | |
| 2013/0251844 | A1 | 9/2013 | Sprenger | |
| 2013/0315990 | A1* | 11/2013 | Bode | A61K 35/741 424/451 |
| 2014/0249103 | A1 | 9/2014 | Buck et al. | |
| 2018/0169122 | A1 | 6/2018 | Hennet et al. | |
| 2018/0185398 | A1 | 7/2018 | Vigsnaes et al. | |

FOREIGN PATENT DOCUMENTS

| WO | 0104341 | 1/2001 |
|---|---|---|
| WO | 2004026257 | 4/2004 |
| WO | 2007101862 | 9/2007 |
| WO | 2009131537 | 10/2009 |
| WO | 2010115934 | 10/2010 |
| WO | 2010115935 | 10/2010 |
| WO | 2011005681 | 1/2011 |
| WO | 2011005681 A1 | 1/2011 |
| WO | 2011100979 | 8/2011 |
| WO | 2011100980 | 8/2011 |
| WO | 2012007588 | 1/2012 |
| WO | 2012009315 | 1/2012 |
| WO | 2012092160 | 7/2012 |
| WO | 2012/106665 A2 | 8/2012 |
| WO | 2012106665 A2 | 8/2012 |
| WO | 2012113404 | 8/2012 |
| WO | 2012113405 | 8/2012 |
| WO | 2012127410 | 9/2012 |
| WO | 2012155916 | 11/2012 |
| WO | 2012156897 | 11/2012 |
| WO | 2012156898 | 11/2012 |
| WO | 2013044928 | 4/2013 |
| WO | 2013091660 | 6/2013 |
| WO | 2013139344 | 9/2013 |
| WO | 2013148134 | 10/2013 |
| WO | 2013154725 | 10/2013 |
| WO | 2013154725 A1 | 10/2013 |
| WO | 2015077233 | 5/2015 |
| WO | 2015157098 | 10/2015 |

OTHER PUBLICATIONS

Thapar et al, Lancet, 2004, 363, 641-53.*
Gavini etal, Microbial Ecology in Health and Disease, 2001, 13, 40-45.*
Yang et al, Alimentary Pharmacology and Therapeutics, 2014, 39, 302-311.*
European Patent Office, "Extended European Search Report", application 15854904.8, dated Jun. 12, 2018, pp. 1-7.
Chaturvedi, P., "Milk Oligosaccharide profiles by reversed-phase HPLC of their perbenzoylated derivatives", Analytical Biochemistry, vol. 251, pp. 89-97; whole document doi:10.1006/abio.1997.2250, (Sep. 1997).
O'Mahony, L. et al., "Lactobacillus and bifidobacterium in irritable bowel syndrome: symptom responses and relationship to cytokine profiles", Gastroenterology, 128:3:541-551: whole document, (Mar. 2005).

(Continued)

Primary Examiner — Ganapathy Krishnan
(74) Attorney, Agent, or Firm — Kunzler Bean & Adamson

(57) ABSTRACT

The application relates to a method for the prophylaxis or treatment of non-infectious diarrhea in a human, the method comprising administering to the human an effective amount of one or more human milk oligosaccharides.

16 Claims, No Drawings

(56) References Cited

OTHER PUBLICATIONS

Silk, D. et al., "Clinical trial: the effects of a trans-galactooligosaccharide prebiotic on faecal microbiota and symptoms in irritable bowel syndrome", Alimentary Pharmacology & Therapeutics, doi:10.1111/j.1365-2036.2008.03911.x, (Nov. 28, 2008).
Walker M. et al., "Duodenal mastoctosis, eosinophilia and intaepithelial lymphocytosis ans possible disease markers in the irritable lowel syndrome and functional dyspepsia", Alimentary Pharmacology & Therapeutics, 29(7_765-773, doi:10.111/j.1365-2036.2009.03937.x, (Apr. 2009).
Buhner, S. et al., "Mast cell-nerve axis with a focus on the human gut", Biochimica et Biophysica Acta, 1822, pp. 85-92, doi:10.1016/j.bbadis.2001.06.004, (2012).
Sikandar, S. et al., "Visceral pain—the ins and Outs, the Ups and Downs", Curr Opin Support Palliat Care, 6(1):17-26, doi:10.1097/SPC.0b013e32834f6ec9, (Mar. 2012).
Kim, G. et al., "Methanobrevibacter smithii is the predominant methanogen in patients with constipation-predominant IBM and methane on breath", Dig Dis Sci, vol. 57, pp. 3213-3218, doi:10.1007/s10620-012-2197-1, (2012).
Bassett, J. et al., "A review of irritable bowel syndrome and an update on therapeutic approaches", Informa Healthcare, Expert Opin. Pharmacother, 9(7):1129-1143, doi:10.1517/14656560802048902, (2008).
Longstreth, G. et al., "Functional bowel disorders", Gastrenterology, vol. 130, pp. 1480-1491, doi:10.1053/j.gastro.2005.11.061, (2006).
Spiller R. et al., "Postinfectious irritable bowel syndrome", Gastroenterology, vol. 136, pp. 1979-1988, doi:10.1053/j.gastro.2009.02.074, (2009).
Guilatre M., et al., "Diarrheoa-predominant IBS patients show mast cell activation and hyperplasia in the jejunum", Gut, vol. 56, pp. 203-209, doi:10.1136/gut.2006.100594, (2007).
Spiller, R. et al., "Guidelines on the irritable bowel syndrome: mechanisms and practical management", Gut, vol. 56, pp. 1770-1798, doi:10.1136/gut.2007.119446, (2007).
Staudacher, H. et al., "Comparision of symptom response following advice for a diet low in fermentable carbohydrates (FODMAPs) verus standard dietary advice in patients with irritable bowel syndrome", Journal of Human Nutrition and Dietetics, vol. 24, pp. 487-495 (2011).
Zhang, L. et al., "Mast cells and irritable bowl syndrome: from the bench to the bedside", Journal of Neurogastroenterology and Motility, 22:2:181-192, (Apr. 2016).
Shulman R. et al., "Increased gastrointestinal permeability and gut inflammation in children with functional abdominal pain and irritable bowel syndrome", J. Pediatr., 153(5):646-650, doi:10.1016/j.jpeds.2008.04.062, (Nov. 2008).
Ohman, L. et al., "Crosstalk at the mucosal border: importance of the gut microenvironment in IBS", Nat, Rev. Gastroenterol., vol. 12, pp. 36-49, doi:10.1038/nrgastro.2014.200, (Jan. 2015).
Qin, J. et al., "A human gut microbial gene catalogue established by metagenomic sequencing", Nature, vol. 464, pp. 59-67, doi:10.1038/nature08821, (Mar. 4, 2010).
Schoepfer, A. et al., "Antibodies to flagellin indicate reactivity to bacterial antigens in IBS patients", Neurogastroenterol Motil, vol. 20, pp. 1110-1118, doi:10.1111/j.1365-2982.2008.01166.x, (2008).
Kerckhoffs, A. et al., "Lower bifidobacteria counts in both duodenal mucosa-associated and fecal microbiota in irritable bowel syndrome patients", World J. Gastroenterol, 15(23):2887-2892, doi:10.3748/wjg.15.2887, (Jun. 21, 2009).
Urashima, T. et al., "Mild Oligosaccharides", Nutrition and Diet Resarch Progress, Nova Biomedical Books, New York, (2011).

Jeffery, I. et al., An irritable bowel syndrome subtype defined by species-specific alterations in faecal microbiota, Gut 2012, 61:997-1006, published on Dec. 16, 2011, doi:10.1136/gutjnl-2011-301501, pp. 997-1006.
Thapar et al., "Diarrhoea in children: an interface between developing and developed countries", the Lancet, vol. 363, Feb. 21, 2004, www.lancet.com, pp. 641-653.
U.S. Appl. No. 15/147,112, Office Action Summary, dated Apr. 21, 2017.
U.S. Appl. No. 15/147,115, Office Action Summary, dated Apr. 21, 2017.
U.S. Appl. No. 15/147,112, Office Action Summary, dated Nov. 24, 2017.
U.S. Appl. No. 15/147,115, Office Action Summary, dated Nov. 27, 2017.
U.S. Appl. No. 15/034,593, Office Action Summary, dated Apr. 20, 2017.
Michael Camilleri, "Peripheral Mechanisms in Irritable Bowel Syndrome", N Engl J. Med. 367;17, Oct. 25, 2012, NEJM.org, pp. 1626-1635.
U.S. Appl. No. 15/034,593, Office Action Summary, dated Nov. 14, 2017.
Rockova, S. "Inter-species differences in the growth of bifidobacteria cultured on human milk oligosaccharides", Folia Microbiologica, 2012, vol. 57, No. 4, Apr. 11, 2012, pp. 321-324.
Heitkemper, M. "Update on Irritable Bowel Syndrome Program of Research", J Korean Academy of Nursing vol. 43 No. 5, 579-586, http://dx.doi.org/10.4040/jkan.2013.43.5.579, Sep. 23, 2013, pp. 579-586.
U.S. Appl. No. 15/897,099, Office Action Summary, dated May 14, 2019, pp. 1-37.
U.S. Appl. No. 15/906,911, Office Action Summary, dated May 14, 2019, pp. 1-38.
U.S. Appl. No. 15/906,911, Final Office Action, dated Dec. 20, 2019, pp. 1-22.
U.S. Appl. No. 15/897,099, Final Office Action, dated Dec. 20, 2019, pp. 1-20.
U.S. Appl. No. 16/706,627, "Office Action Summary", dated May 29, 2020, pp. 1-26.
China PTO, "Notification of the First Office Action", dated Mar. 28, 2019, pp. 1-7.
Europe PTO, "Communication pursuant to Article 94(3) EPC", dated Dec. 12, 2019, pp. 1-3.
L. O'Mahony et al., "Lactobacillus and Bifidobacterium in Irritable Bowel Syndrome: Symptom Responses and Relationship to Cytokine Profiles", Gastroenterology 2005;128:pp. 541-551.
E. Elison et al., "Oral supplementation of healthy adults with 2!-O-fucosyllactose and lacto-N-neotetraose is well tolerated and shifts the intestinal microbiota", British Journal of Nutrition, Aug. 22, 2016, pp. 1-13.
G. Gibson et al., "The International Scientific Association for Probiotics and Prebiotics (ISAPP) consensus statement on the definition and scope of prebiotics", Nature Reviews | Gastroenterology & Hepatology, vol. 14, Aug. 2017, pp. 491-502.
D. Barile et al., "Human milk and related oligosaccharides as prebiotics", Biotechnology, ScienceDirect, Feb. 19, 2013, pp. 214-219.
M. Haarman et al., "Quantitative Real-Time PCR Assays to Identify and Quantify Fecal *Bifidobacterium* Species in Infants Receiving a Prebiotic Infant Formula", Applied and Environmental Microbiology, vol. 71 No. 5, May 2005, p. 2318-2324.
N. Sprenger et al., "Longitudinal change of selected human milk oligosaccharides and association to infants' growth, an observatory, single center, longitudinal cohort study", PLOS One, Feb. 9, 2017, pp. 1-15.
U.S. Appl. No. 15/897,099, Office Action Summary, dated Jul. 24, 2020, pp. 1-34.
U.S. Appl. No. 15/906,911, Office Action Summary, dated Jul. 24, 2020, pp. 1-34.

\* cited by examiner

COMPOSITION COMPRISING HMSS/HMOS AND USE THEREOF

CROSS-REFERENCES TO RELATED APPLICATIONS

This is a continuation-in-part application of and claims priority to, U.S. application Ser. No. 15/147,112 entitled "COMPOSITION COMPRISING HMSs/HMOs AND USE THEREOF" and filed on May 5, 2016 for Thierry Hennet et al. and to U.S. patent application Ser. No. 15/034,593 entitled SYNTHETIC COMPOSITION AND METHOD FOR TREATING IRRITABLE BOWEL SYNDROME and filed on May 5, 2016 for Thierry Hennet et al., and claims the priority to PCT/DK2015/050332 entitled SYNTHETIC COMPOSITION AND METHOD FOR TREATING IRRITABLE BOWEL SYNDROME and filed on Oct. 29, 2015 for Thierry Hennet and claims priority to Denmark Application No. PC 2014 7063 which are incorporated herein by reference.

FIELD OF THE INVENTION

This invention relates to compositions and methods employing human milk components for the treatment of non-infectious diarrhea.

BACKGROUND

Description of the Related Art

Diarrhea affects most individuals at some time during their lives. It results when the efficiency of the intestine for absorbing water, electrolytes, and nutrients is impaired. Approximately 8-9 litres of fluid enters the intestines daily of which 1-2 litres represents food and liquid intake, and the rest is from endogenous sources such as salivary, gastric, pancreatic, biliary, and intestinal secretions. Most of the fluid, about 6-7 litres, is absorbed in the small intestine, and only about 1-2 litres is presented to the colon. Most of this is absorbed as it passes through the colon, leaving a stool output of about 100-200 g/day. Therefore, small changes in this absorption efficiency can radically change the wetness of the stool. A great variety of drugs, toxins, pathogens, and foodstuffs can impair the efficiency of electrolyte and water absorption, leading to diarrhea.

Normal bowel frequency ranges from three times a day to three times a week in the healthy population. Diarrhea is the increased frequency of stooling, with stool consistency less solid than normal. Acute \diarrhea is defined as three or more stools per day of decreased form from the normal, lasting for less than 14 days. If the duration of symptoms is longer than 1 month, it is considered chronic diarrhea. Most cases of acute diarrhea are self-limited, caused by infectious agents (e.g. viruses, bacteria, parasites), and do not require medication unless the patient is immunocompromised.

Mechanistically, absorption may be impaired by poorly absorbed, osmotically active solutes in the intestinal lumen, by alteration in absorptive cell function, by increases in crypt cell secretion, and by too rapid transit of intestinal contents. Most often, absorption is impaired by mechanisms acting in concert. For example, excessive volume of intestinal contents can speed intestinal transit; cytokines from epithelial inflammatory cells can enhance cryptal secretion, and can influence the enteric nervous system to speed transit; bile salts, and long-chain fatty acids, malabsorbed in the small intestine, can block water and electrolyte absorption in the colon. The colon employs several mechanisms to ensure it delivers to the recto sigmoid colon a formed stool, probably the most important factor in faecal continence. The colon has reserve capacity by which it can absorb 2-3 extra litres of water and electrolytes delivered from the small intestine in a day. Colonic bacteria ferment soluble carbohydrate and protein, which escaped small intestinal absorption, into absorbable gases and short-chain fatty acids. Otherwise, these unfermented, unabsorbable solutes would be osmotically active in colonic contents, and would cause diarrhea.

Most cases of diarrhea, especially acute diarrhea, are infection related; especially due to *Campylobacter, Salmonella, Shigella, E. coli, Vibrio* and *Aeromonas* organisms. In most cases, the diarrhea resolves itself within 48 hours and no treatment other than rehydration is needed. Causes of non-infectious diarrhea include inflammatory bowel disease, irritable bowel syndrome, ischemic bowel disease, partial small bowel obstruction, pelvic abscess in the recto sigmoid area, faecal impaction, carcinoid syndrome, food allergies, lactose intolerance, the ingestion of poorly absorbable sugars such as lactulose, acute alcohol ingestion, and adverse effects of prescription medication; often antibiotics. Non-infectious diarrhea is often persistent, chronic and difficult to treat. Common treatments include anti-motility agents like Loperamide to reduce the number of stools, bile acid sequestrants, digestive enzymes containing lactase, probiotics, etc.

Non-infectious diarrhea is particularly common in irritable bowel syndrome (IBS) patients. Irritable bowel syndrome is a clinically heterogeneous disorder of human patients, particularly adult, with chronic symptoms such as abdominal pain, abdominal discomfort, abdominal bloating, fatigue, and changes in bowel movement patterns, such as patterns of loose or more frequent bowel movements, diarrhea and constipation. Routine clinical tests on patients typically show no abnormalities, although their bowels may be more sensitive to certain stimuli, such as balloon insufflation testing. The worldwide prevalence of IBS is about 10-20% (Longstreth et al. *Gastroenterology* 130, 1480 (2006)) but may be higher in certain countries. The causes of IBS are unknown but disruptions of the brain-gut axis, acute gastrointestinal infections, small intestinal bacterial overgrowths, antibiotic usages and dysbiosis are thought to be important risk factors (Kim et al. *Digest. Dis. Sci.* 57, 3213 (2012)). Other risk factors are young age, prolonged fever, anxiety, and depression. Chronic low-grade inflammation commonly occurs in IBS patients, but there are otherwise little or no observable clinical manifestations.

Diagnosis of IBS is difficult. No biomarker-based tests can be performed to diagnose IBS. Diagnosis generally involves excluding conditions that produce IBS-like symptoms and then following a procedure to categorise a patient's symptoms. Ruling out parasitic infections, lactose intolerance, and celiac disease is recommended for all patients before a diagnosis of IBS is made. Once diagnosed, patients are usually classified in accordance with the Rome III criteria into four symptom subtypes based on stool consistency: diarrhea predominant (IBS-D), constipation predominant (IBS-C), mixed subtype (IBS-M) with alternating episodes of both diarrhea and constipation, and unsubtyped IBS (IBS-U).

There is no cure for IBS and current treatments focus on attempting to relieve symptoms. Treatments take various forms such as dietary adjustments, medication, and psychological interventions. Patient education and good doctor-patient relationships are also important. However, most treatment is unsatisfactory and most patients continue to experience chronic pain, fatigue, and other symptoms. While IBS has no direct effect on life expectancy, its high prevalence and significant effects on quality of life make it a condition with a high social cost. The general hopelessness associated with IBS is a source of frustration for both patients and health care practitioners treating them.

Current research has implicated the gastrointestinal microbiota, the brain-gut axis and the mast cells in the pathophysiology of IBS. The human gastrointestinal microbiota includes at least 1,000 species of bacteria, and about $10^{14}$ individual bacterial cells from about 160 different species inhabit each individual's intestine (Qin et al. *Nature* 464, 59 (2010)). It is believed that an individual's genetic make-up and acquired immunity, as well as environmental factors, influence their gastrointestinal microbiota. The microbiota in turn shape the individual's immunity and physiology within the gastrointestinal system. It is also believed that a healthy individual maintains a symbiotic relationship with the microbiota colonizing his/her intestines, while an individual with IBS has an imbalance in this microbiota-host interaction.

Treatments that target gastrointestinal microbiota such as antibiotics, probiotics and prebiotics appear to alleviate the symptoms of IBS; at least temporarily. For instance, the antibiotic rifaximin appears to reduce bowel movement in IBS-D patients.

Abdominal pain and discomfort associated with IBS is connected to the brain-gut axis and the response to stress hormones. IBS patients typically experience abnormal gut motility and visceral hypersensitivity mediated by the brain-gut axis or central stress response system. One arm of the brain-gut axis is the central efferent pathway, which is formed by the sympathetic nervous system and the hypothalamic-pituitary-adrenal axis (HPA). In stress-sensitive disorders including IBS, stress hormones of the HPA axis, such as adrenocorticotropic hormone (ACTH), cortisol, and catecholamine are released. Some studies have shown that the HPA axis response in IBS patients is caused by increased mucosal immune activation, which in turn increases plasma cytokine levels to stimulate the HPA axis.

In addition to the gut microbiome and the gut-brain axis, the mast cells may also play an important role in the pathogenesis of IBS. Increased mast cell infiltration and activation in distal gut segments are associated with symptom onset and severity of IBS. These cells are also implicated in the elevated response of visceral afferent nerves to mucosal stimulus in IBS patients. Mast cell hyperplasia is commonly observed following infection by bacteria in both post-infectious IBS and non-post-infectious IBS.

A recent development in IBS treatment has been the low FODMAP diet. This diet requires patients to restrict the intake of FODMAP carbohydrates. These are Fermentable Oligo-, Di-, Monosaccharides and Polyols which are poorly absorbed in the proximal small intestine, osmotically active, and fermented by intestinal bacteria in which some produce hydrogen. Adherence to this diet has resulted in symptom improvements for some patients (Staudacher et al. *J. Hum. Nutr. Diet.* 24, 487 (2011)). However, some of the FODMAP carbohydrates are beneficial fibres, and foods that contain them are common, highly nutritious fruits, vegetables and legumes.

Similarly, for lactose intolerance, there is no universally accepted therapy for treatment. However, existing strategies for management of the conditions include avoidance of lactose-containing dairy foods (milks, soft cheeses and ice creams) and consuming lactase prior to a meal containing lactose. Although restricting dietary lactose may improve gastrointestinal complaints, long-term effects of a diet low or free of dairy products can be of concern, since dairy products provides a package of essential nutrients such as calcium, protein, riboflavin, vitamin A and vitamin D. Dietary calcium is an important part of the recommended daily allowance of vitamins and minerals, and for many people it is not possible to achieve recommended daily calcium intakes with a dairy low or free diet. It has been observed that deficiency in calcium can lead to increased risk of osteoporosis, hypertension and possibly cancer.

Lactase drugs are effective and are available without prescription. However, they do need to be consumed before meals containing lactose. Also, although uncommon, they may provoke serious, allergy-related side effects.

Therefore, there is a need for a safe, effective intervention for the treatment of non-infectious diarrhea.

SUMMARY

This invention provides synthetic compositions comprising one or more human milk monosaccharides (HMSs) or one or more human milk oligosaccharides (HMOs), or both, that can be advantageously used for prophylaxis or treatment of non-infectious diarrhoea in a human, in particular a non-infant human individual.

Accordingly: a first aspect of this invention relates to a human milk mono- or oligosaccharide or a mixture of human milk mono- and/or oligosaccharides for the prophylaxis or treatment of non-infectious diarrhoea in a human;

a second aspect of this invention relates to a human milk mono- or oligosaccharide or a mixture of human milk mono- and/or oligosaccharides for the prophylaxis or treatment of non-infectious diarrhoea in an irritable bowel syndrome patient, lactose intolerant patient and/or a patient having undergone antibiotic treatment;

a third aspect of this invention relates to a synthetic composition for the prophylaxis or treatment of non-infectious diarrhoea in a human, the composition comprising an effective amount of one or more human milk monosaccharides or one or more human milk oligosaccharides, or both;

a fourth aspect of this invention relates to a synthetic composition for the prophylaxis or treatment of non-infectious diarrhoea in an irritable bowel syndrome patient, lactose intolerant patient and/or a patient having undergone antibiotic treatment, the composition comprising an effective amount of one or more human milk monosaccharides or one or more human milk oligosaccharides, or both;

a fifth aspect of this invention provides a method for the prophylaxis or treatment of non-infectious diarrhoea in a human, the method comprising administering to the human an effective amount of one or more human milk monosaccharides or one or more human milk oligosaccharide, or both;

a sixth aspect of this invention provides a method for the prophylaxis or treatment of non-infectious diarrhoea in an irritable bowel syndrome patient, lactose intolerant patient and/or a patient having undergone antibiotic treatment, the method comprising administering to the human an effective amount of one or more human milk monosaccharides or one or more human milk oligosaccharides, or both.

Preferably the amount of a human milk mono- and/or oligosaccharide is effective to increase (i) the abundance, particularly the relative abundance, of bifidobacteria, and/or (ii) the beta-galactosidase activity, in the gastrointestinal tract of the human. More preferably, the bifidobacteria increased is a member of the phylogenetic *Bifidobacterium adolescentis* group, for example, *Bifidobacterium pseudocatenulatum* and/or *Bifidobacterium adolescentis*.

The patient may have intestinal dysbiosis and/or an impaired mucosal barrier.

Preferably, the human milk oligosaccharide is 2'-FL, 3-FL, DFL, LNnT, LNT, 3'-SL, 6'-SL or LNFP-I or a mixture thereof. For example, the composition can comprise a mixture of a fucosylated HMO such as 2'-FL and a non-fucosylated neutral HMO such as LNnT or LNT, or both. 2'-FL and LNnT/LNT may be present in a mass ratio of about 5:1 to 1:1; more preferably about 4:1 to 2:1.

The synthetic composition can be a nutritional or pharmaceutical composition. Preferably, synthetic composition of the invention is administered daily. Furthermore, the synthetic composition is preferably administered for a period of at least one month, such as at least 2 months or for a longer period of time, for example chronically on an ongoing basis.

The synthetic composition may be administered to the human or patient as a daily dose of about 1 g to about 15 g such as from about 3 g to about 10 g of HMSs and/or HMOs. The patient can be administered a higher amount, preferably 5 g to 10 g per day, of the HMSs and/or HMOs for an initial treatment period, followed by a lower amount, preferably 1 g to 5 g per day, for a maintenance period. The initial treatment period can be 1 to 8 weeks. The maintenance period is at least 1 month.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

DETAILED DESCRIPTION

It has been surprisingly found that human milk monosaccharides (HMSs) and/or human milk oligosaccharides (HMOs) are able to decrease bowel movement frequency and improve stool consistency in patients suffering from non-infectious diarrhoea, particularly those who are suffering from intestinal dysbiosis or an impaired mucosal barrier. HMSs and/or HMOs preferentially increase the abundance of bifidobacteria in the gastro-intestinal tract, metabolising carbohydrates, in particular, which escaped absorption in the small intestine, into lactate and short-chain fatty acids, making them less osmotically active in the colon. Further, HMSs and/or HMOs act to reduce chronic mucosal inflammation and/or repair damage to the mucosal barrier, potentially reducing cryptal secretion. HMSs and/or HMOs can also act on neuronally dependent gut migrating motor complexes to address disorders of gut motility and possibly have beneficial effects on the central nervous systems of patients. As an outcome, bowel movement frequency is decreased and stool consistency improved.

The term "oral administration" preferably means any conventional form for the oral delivery of a composition to a patient that causes the deposition of the composition in the gastrointestinal tract (including the stomach) of the patient. Accordingly, oral administration includes swallowing of composition by the patient, enteral feeding through a nasogastric tube, and the like.

The term "effective amount" preferably means an amount of a composition that provides a human milk monosaccharide or human milk oligosaccharide in a sufficient amount to render a desired treatment outcome in a patient. An effective amount can be administered in one or more doses to the patient to achieve the desired treatment outcome.

The term "human milk monosaccharide" or "HMS" preferably means a monosaccharide found in human breast milk. Examples include sialic acid and L-fucose. In human milk, the sialic acid is N-acetylneuraminic acid.

The term "human milk oligosaccharide" or "HMO" preferably means a complex carbohydrate found in human breast milk that can be in acidic or neutral form. More than about 200 different HMO structures are known to exist in human breast milk (Urashima et al.: *Milk Oligosaccharides*, Nova Biomedical Books, New York, 2011). HMOs can be backbone, fucosylated and sialylated oligosaccharides. Backbone HMOs consists of Glu, Gal and GlcNAc and are devoid of Fuc and sialic acid. Examples of backbone HMOs include lacto-N-tetraose (LNT), lacto-N-neotetraose (LNnT), lacto-N-neohexaose (LNnH) and lacto-N-hexaose (LNH). Fucosyl HMOs are fucosylated lactoses or fucosylated backbone HMOs such as 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose III (LNFP-III), fucosyl-para-lacto-N-neohexaose (F-pLNnH), lacto-N-difucohexaose I (LNDFH-I), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-lacto-N-hexaose III (FLNH-III) and fucosyl-para-lacto-N-neohexaose (F-pLNnH). Sialyl HMOs are sialylated lactoses or sialylated backbone HMOs such as 3',6-disialyllacto-N-tetraose (DSLNT), 6'-sialyllactose (6'-SL), 3'-sialyllactose (3'-SL), 6'-sialyllacto-N-neotetraose (LST c), 3'-sialyllacto-N-tetraose (LST a) and 6-sialyllacto-N-tetraose (LST b). HMOs containing both sialyl and fucosyl groups may be considered to belong to either of the latter two groups. Examples for sialyl and fucosyl HMOs include disialyl-fucosyl-lacto-N-hexaose II (DSFLNH-II), fucosyl-sialyl-lacto-N-neohexaose I (FSLNnH-I), fucosyl-sialyl-lacto-N-hexaose I (FSLNH-I) and 3-fucosyl-3'-sialyllactose (FSL).

The terms "microbiota", "microflora" and "microbiome" preferably mean a community of living microorganisms that typically inhabits a bodily organ or part. The most dominant members of the gastrointestinal microbiota include microorganisms of the phyla of *Firmicutes, Bacteroidetes, Actinobacteria, Proteobacteria, Synergistetes, Verrucomicrobia, Fusobacteria*, and *Euryarchaeota*; at genus level the microorganisms of *Bacteroides, Faecalibacterium, Bifidobacterium, Roseburia, Alistipes, Collinsella, Blautia, Coprococcus, Ruminococcus, Eubacterium* and *Dorea*; and at species level microorganisms of *Bacteroides uniformis, Alistipes putredinis, Parabacteroides merdae, Ruminococcus bromii, Dorea longicatena, Bacteroides caccae, Bacteroides*

*thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. In some instances, the gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

The terms "irritable bowel syndrome" and "IBS" preferably mean a group of functional bowel disorders of humans, particularly adults, characterized by one or more chronic symptoms including abdominal pain, abdominal discomfort, abdominal bloating, fatigue, and changes in bowel movement patterns, such as patterns of loose or more frequent bowel movements, diarrhoea and constipation, typically in the absence of any apparent structural abnormality. There are at least three forms of IBS, depending on which symptom predominates: (1) diarrhoea-predominant (IBS-D); (2) constipation-predominant (IBS-C); and (3) IBS with alternating stool pattern (IBS-A or IBS-M). There are also various clinical subtypes of IBS, such as post-infectious IBS (IBS-PI).

The term "bifidobacteria" means a member of the *Bifidobacterium* genus commonly found in the human gastro-intestinal tract. Examples of bifidobacteria are: *Bifidobacterium longum, Bifidobacterium bifidum*, and members of the phylogenetic *Bifidobacterium adolescentis* group. In non-infant humans, bifidobacteria preferably include members of the phylogenetic *Bifidobacterium adolescentis* group, for example, *Bifidobacterium pseudocatenulatum* and/or *Bifidobacterium adolescentis*.

The term "synthetic composition" means a composition which is artificially prepared and preferably means a composition containing at least one compound that is produced ex vivo chemically and/or biologically, e.g. by means of chemical reaction, enzymatic reaction or recombinantly. In some embodiments a synthetic composition may be, but preferably is not, identical with a naturally occurring composition. The synthetic composition typically comprises one or more compounds HMSs and/or HMOs that are capable of preferentially increasing the abundance of bifidobacteria. In some embodiments, the synthetic composition may comprise one or more compounds or components other than HMSs and/or HMOs that may have an effect on bifidobacteria of a human subject microbiota in vivo, e.g. non-digestible oligosaccharides or prebiotics. Also in some embodiments, the synthetic compositions may comprise one or more nutritionally or pharmaceutically active components which do not affect adversely the efficacy of the above mentioned compounds. Some non-limiting embodiments of a synthetic composition of the invention are also described below.

The term "relative abundance of bifidobacteria" means the abundance of bifidobacteria relative to other genus in the microbiota of the gastro-intestinal tract.

The term "relative growth of bifidobacteria" means the growth of bifidobacteria relative to other genus in the microbiota in the gastro-intestinal tract.

The term "non-infant human" or "non-infant" means in the present context a human of 3 years of age and older. A non-infant human can be a child, a teenager, an adult or an elderly.

The term "enteral administration" means any conventional form for delivery of a composition to a human that causes the deposition of the composition in the gastrointestinal tract (including the stomach). Methods of enteral administration include feeding through a naso-gastric tube or jejunum tube, oral, sublingual and rectal.

The term "oral administration" means any conventional form for the delivery of a composition to a human through the mouth. Accordingly, oral administration is a form of enteral administration.

The term "about" in the present context means up to 2.5% deviation from the corresponded value.

The term "preferably" is used herein to indicated the best mode of invention, but to limit the scope of invention.

HMSs and/or HMOs for Prophylaxis or Treatment of Non-Infectious Diarrhoea in a Human HMSs and/or HMOs for prophylaxis or treatment of non-infectious diarrhoea in a human may be a single HMS, a mixture of HMSs, a single HMO, a mixture of any HMOs or a mixture of one or more HMSs and one or more HMOs suitable for the purpose of the invention. Preferably, the HMS is L-fucose or sialic acid, and the HMO is a fucosylated or a non-fucosylated neutral HMO. More preferably, the HMSs and/or HMOs for prophylaxis or treatment of non-infectious diarrhoea in a human is a mixture of at least a first HMO, at least a second HMO and optionally L-fucose and/or sialic, wherein the first HMO is a fucosylated neutral HMO and the second HMO is a non-fucosylated neutral HMO. Particularly, the mixture may contain a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. Preferably, the mixture contains a fucosylated HMO selected from the list consisting of 2'-FL, 3-FL and DFL, and a non-fucosylated HMO selected from the list consisting of LNT and LNnT; advantageously the mixture comprises 2'-FL and LNnT and/or LNT. In some embodiments, the mixture may essentially consist of two neutral HMOs, e.g. a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. Preferably, the mixture essentially consists of a fucosylated HMO selected from the list consisting of 2'-FL, 3-FL and DFL, and a non-fucosylated HMO selected from the list consisting of LNT and LNnT; in one preferred embodiment the mixture essentially consists of 2'-FL and LNnT, in another preferred embodiment the mixture essentially consists of 2'-FL and LNT.

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified E. coli.

Synthetic Composition Comprising HMSs and/or HMOs

The synthetic composition may comprise a single HMS, a mixture of HMSs, a single HMO, a mixture of any HMOs or a mixture of one or more HMSs and one or more HMOs suitable for the purpose of the invention. Preferably, the HMS is L-fucose or sialic acid, and the HMO is a fucosylated or a non-fucosylated neutral HMO. More preferably, the composition comprises a mixture of at least a first HMO, at least a second HMO and optionally L-fucose and/or sialic, wherein the first HMO is a fucosylated neutral HMO and the second HMO is a non-fucosylated neutral HMO. Particularly, the composition may contain a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. Preferably, the composition contains a fucosylated HMO selected from the list consisting of 2'-FL, 3-FL and DFL, and a non-fucosylated HMO selected from the list consisting of LNT and LNnT, advantageously the composition comprises 2'-FL and LNnT and/or LNT. In some embodiments, the composition comprises a mixture essentially consisting of two neutral HMOs, e.g. a fucosylated HMO selected from the list consisting of 2'-FL, 3-FL, DFL, LNFP-I, LNFP-II, LNFP-III, LNFP-V, LNDFH-I, LNDFH-II, LNDFH-III, FLNH-I, FLNH-II, FLNnH, FpLNH-I and F-pLNnH II, and a non-fucosylated HMO selected from the list consisting of LNT, LNnT, LNH, LNnH, pLNH and pLNnH. Preferably, the composition comprises a mixture consisting of a fucosylated HMO selected from the list consisting of 2'-FL, 3-FL and DFL, and a non-fucosylated HMO selected from the list consisting of LNT and LNnT; in one preferred embodiment the composition comprises a mixture essentially consisting of 2'-FL and LNnT, in another preferred embodiment the composition comprises a mixture essentially consisting of 2'-FL and LNT.

A synthetic composition of this invention comprising one or more human milk monosaccharides or one or more human milk oligosaccharides, or both, can take any suitable form. For example, the composition can be in the form of a nutritional composition which contains other macronutrients such as proteins, lipids or other carbohydrates. The synthetic composition can also be a pharmaceutical composition.

Nutritional Compositions

A nutritional composition of this invention can contain sources of protein, lipids and/or digestible carbohydrates and can be in powdered or liquid forms. The composition can be designed to be the sole source of nutrition or a nutritional supplement. For IBS patients, a nutritional supplement is preferred; especially a supplement which can form a meal or snack replacement. Preferably the nutritional composition is lactose-reduced or, better yet, lactose-free. Preferably, the nutritional composition is also free from, or low in amounts of, FODMAP carbohydrates.

Suitable protein sources include milk proteins, soy protein, rice protein, pea protein and oat protein, or mixtures thereof. Milk proteins can be in the form of milk protein concentrates, whey protein or casein, or mixtures of both. Soy, rice, pea and oat protein can be in the form or protein isolated. The protein can be whole protein or hydrolysed protein, either partially hydrolysed or extensively hydrolysed. The protein can provide about 5% to about 50%, preferably about 10% to 30%, of the energy of the nutritional composition. The protein source preferably is not a source of non-fermentable carbohydrates such as lactose. Therefore, if a milk protein is used as the protein source, the milk protein is preferably lactose-reduced or lactose-free.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the GI tract and can reduce permeability. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, tapioca, sucrose, and glucose, or mixtures thereof. Generally digestible carbohydrates provide about 35% to about 75%, preferably about 45% to 70%, of the energy of the nutritional composition. Preferably the digestible carbohydrate is free from lactose.

Suitable lipids include rapeseed oil, sunflower seed oil, palm oil, soy oil, milk fat, corn oil and soy lecithin. Long-chain poly unsaturated fatty acids (LC-PUFA), especially omega-3 fatty acids such as docosahexaenoic acid (DHA), can be included in the lipid source because they have anti-inflammatory properties. Suitable sources of LC-PUFA are plant oils, marine plankton oils, fungal oils, and fish oils. The lipid source can also include medium chain triglycerides (MCT). Fractionated coconut oils are a suitable source of medium chain triglycerides. The lipid source preferably provides about 5% to about 25% of the energy of the nutritional composition; for example, about 10% to 20%. The lipid content is preferably reduced because high fat diets can provoke IBS symptoms.

The nutritional composition may also include vitamins and minerals. If the nutritional composition is intended to be a sole source of nutrition, it preferably includes a vitamin and mineral profile, preferably a complete vitamin and mineral profile. The term "complete" in the present context means a vitamin and mineral profile comprising all vitamins and minerals essential for body function, wherein the essential vitamins includes at least 9 vitamins from the exemplary group below, such as 10, 11, 12 or 13, or more, and the essential minerals includes at least 5 minerals from the exemplary group below, such as from 6 to 13 or more. Examples of vitamins include vitamins A, B-complex (such as B1, B2, B6 and B12), C, D, E and K, niacin and acid vitamins such as pantothenic acid and folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 µg/ml to about 10 µg/ml. Lutein can be included in an amount of from about 0.001 µg/ml to about 10 µg/ml, preferably from about 0.044 µg/ml to about 5 g/ml of lutein. Lycopene can be included in an amount from about 0.001 µg/ml to about 10 µg/ml, preferably about 0.0185 mg/ml to about 5 g/ml of lycopene. Beta-carotene can comprise from about 0.001 µg/ml to about 10 mg/ml, for example about 0.034 µg/ml to about 5 µg/ml of beta-carotene.

The nutritional composition can also contain various other conventional ingredients such as preservatives, emulsifying agents, thickening agents, buffers, fibres and probiotics, especially probiotics which can help to reduce symptoms in IBS patients (e.g. VSL#3, *B. infantis* 35624, *B. animalis* subsp. *lactis* BB-12, *B. lactis* Bi-07, *L. rhamnosus* GG, *L. rhamnosus* Lc705, *L. plantarum* DSM 9843, *L. plantarum* CECT7484, *L. plantarum* CECT7485, *L. acidophilus* NCFM, *L. fermentum* CECT5716, *B. breve* Bb99, *Propionibacterium freundenreichii* ssp. *Shermanii* JS, *P. acidilactici* CECET7483, *Streptococcus faecium*), antioxidant/anti-inflammatory compounds including tocopherols, caroteinoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be in the form of a soluble powder, a liquid concentrate, or a ready-to-use formulation. Various flavours, fibres and other additives can also be present.

The nutritional compositions can be prepared by any commonly used manufacturing techniques for preparing nutritional compositions in solid or liquid form. For example, the composition can be prepared from various feed solutions. A protein-in-fat feed solution can be prepared by heating and mixing the lipid source and then adding an emulsifier (e.g., lecithin), fat soluble vitamins, and at least a portion of the protein source while heating and stirring. A carbohydrate feed solution is also prepared by adding minerals, trace and ultra trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packaged to form an aseptically packaged nutritional composition. In this form, the nutritional composition can be in ready-to-feed or concentrated liquid form. Alternatively, the composition can be spray dried and processed and packaged as a reconstitutable powder.

When the nutritional product is a ready-to-feed nutritional liquid, the total concentration of HMOs in the liquid, by weight of the liquid, is from about 0.02% to about 2.0%, including from about 0.1% to about 1.5%, including from about 0.3% to about 1.0%. When the nutritional product is a concentrated nutritional liquid, the total concentration of HMOs in the liquid, by weight of the liquid, is from about 0.04% to about 4.0%, including from about 0.2% to about 3.0%, including from about 0.6% to about 2.0%.

Unit Dosage Forms

The synthetic composition can also be in a unit dosage form such as a capsule, tablet or sachet. For example, the composition can be in a tablet form comprising the human milk mono-and/or oligosaccharides, and one or more additional components to aid formulation and administration, such as diluents, excipients, antioxidants, lubricants, colorants, binders, disintegrants, and the like.

Suitable diluents, excipients, lubricants, colorants, binders, and disintegrants include polyethylene, polyvinyl chloride, ethyl cellulose, acrylate polymers and their copolymers, hydroxyethyl-cellulose, hydroxypropylmethyl-cellulose (HPMC), sodium carboxymethylcellulose, polyhydroxyethyl methacrylate (PHEMA), polyvinyl alcohol (PVA), polyvinyl pyrrolidone (PVP), polyethylene oxide (PEO), or polyacrylamide (PA), carrageenan, sodium alginate, polycarbophil, polyacrylic acid, tragacanth, methyl cellulose, pectin, natural gums, xanthan gum, guar gum, karaya gum, hypromellose, magnesium stearate, microcrystalline cellulose, and colloidal silicon dioxide. Suitable antioxidants are vitamin A, carotenoids, vitamin C, vitamin E, selenium, flavonoids, polyphenols, lycopene, lutein, lignan, coenzyme Q10 ("CoQIO") and glutathione.

The unit dosage forms, especially those in sachet form, can also include various nutrients including macronutrients.

The unit dosage forms can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated so as to provide sustained, delayed or controlled release of the mixture therein.

The unit dosage forms can also be administered by rectal suppository, aerosol tube, naso-gastric tube or direct infusion into the GI tract or stomach.

The unit dosage forms can also include therapeutic agents such as antiviral agents, antibiotics, probiotics, analgesics, and anti-inflammatory agents. The synthetic composition in unit dosage form may be a pharmaceutical composition or a nutritional supplement.

Administration Dosing

For reducing symptoms of non-infectious diarrhoea in a patient, the amount of HMS(s) and/or HMO(s), preferably HMO(s), required to be administered to the patient will vary depending upon factors such as the risk and severity of the disease, the age of the patient, the form of the composition, and other medications being administered to the patient. However, the required amount can be readily set by a medical practitioner and would generally be in the range from about 200 mg to about 20 g per day, in certain embodiments from about 1 g to about 15 g per day, from about 3 g to about 10 g per day, in certain embodiments from about 3 g to about 7.5 g per day. An appropriate dose can be determined based on several factors, including, for example, body weight and/or condition, the severity of the condition, being treated or prevented, other ailments and/or diseases, the incidence and/or severity of side effects and the manner of administration. Appropriate dose ranges may be determined by methods known to those skilled in the art. During an initial treatment phase, the dosing can be higher or lower depending upon the need to boost bifidobacteria abundance or initial tolerance to HMSs/HMOs. During a maintenance phase, the dosing can be set for chronic long term use.

The duration of the HMS/HMO administration will vary depending upon factors such as the risk and severity of the medical condition, age, the form of the composition, the dose and other medications being administered. However, the duration can be readily set by a medical practitioner.

Generally, a duration of at least a week will be required to sufficiently to impact symptoms. For example, the duration may be for 1 to 3 months, or longer. The administration can continue chronically for an indefinite period.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

EXAMPLES

Examples below are to illustrate non-limiting embodiments of the invention.

Example 1—Human Trial in IBS-D Patients

A total of 60 male and female IBS-D patients are recruited to participate in the study. After a screening visit and run-in period of 1-2 weeks, the patients are selected. The patients are randomized into three groups, each of 20 patients, with two groups consuming the treatment product and one group the placebo product for 8 weeks. The treatment product contains either 5 or 10 grams of a combination of 2'-FL and LNnT in a 4:1 ratio while the control product contains 2 grams of glucose. Both products are in powder form in a unit dosage container.

The patients are eligible to participate if: they are between 18 and 60 years of age; meet the Rome III criteria for IBS-D; report a weekly average of worst daily abdominal pain intensity score of ≥3 on a 0-10 point scale; report a pain/discomfort frequency of at least 2 days a week during screening evaluation; report at least one stool with a consistency of Type 6 or Type 7 Bristol stool (BSS) on at least 2 days per week. All recruited patients are able and willing to understand and comply with the study procedures. Patients are excluded if: they have participated in a clinical study one month prior to screening visit; they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 3 months prior to the study; consumed antibiotic drugs 3 months prior to the study; consumed on a regular basis any medication that might interfere with symptom evaluation 2 weeks prior to the study; and pregnant or lactating.

At the initial visit (screening), each patient is given both written and oral information about the study and the patient is asked to sign an informed consent form.

Patients are evaluated by a full review of clinical history, and based on clinical symptoms, IBS-D patients are enrolled.

A blood sample for eligibility analysis is collected. A talk through of the electronic questionnaires (GSRS, IBS-SSS, QoL and BSFS) is performed to familiarise the patients with the electronic system, and equipment for faecal sampling is distributed to each patient. Patients are instructed to keep their samples in the freezer until the next visit.

At the second visit (beginning of intervention), eligibility criteria are checked and eligible subjects are randomised to the two arms in the trial. Symptoms (as measured by GSRS, IBS-SSS, BSFS and QoL scales) are assessed. Trial supplementation is distributed along with instructions on use of an electronic compliance diary. The faecal samples are collected and equipment for collecting new samples are distributed. Patients are reminded not to change their usual diet during the study.

Blood samples are collected for biomarker studies and biobanking. The serum from the blood samples is transferred to cryotubes and stored at −80° C. The following biomarkers are measured TNF-α, IL-1β, IL-8, IL-6, IL-12, IL-10, MIP-1β, hs-CRP, lipopolysaccharide binding protein, tryptase, antiflagellin, zonulin, histamine, prostaglandin 2, and cortisol.

The faecal samples are stored at −80° C. until analysis. Microbiological analysis is performed on the faecal samples using the 16S rRNA gene sequence.

The study runs for 8 weeks with the patients consuming either a placebo or a treatment product daily. Patients are instructed to consume the products in the morning with breakfast. Compliance is monitored through the interactive internet enabled system. The patients also use the system to record:

Bristol Stool Form Scale (BSFS) information,
symptom information such as abdominal pain, abdominal discomfort, abdominal cramping, abdominal bloating, and abdominal fullness,
Quality of life (QoL) information,
IBS severity scoring system (IBS-SSS) information,
Additional Gastrointestinal Symptom Rating Scale (GSRS) information.

This questionnaire includes 15 items covering five dimensions (abdominal pain, indigestion, reflux, diarrhoea, constipation) and uses a seven-graded Likert scale.

4 weeks after commencement, there is an intermediate check. A physical examination is done and symptoms (as measured by GSRS, IBS-SSS, BSFS and QoL scales etc.) are reassessed. Faecal samples and blood samples are collected and analysed as before, and equipment for collection of new faecal samples are distributed.

At the end of the intervention (8 weeks), each patient has a visit with the medical team. A physical examination is done and symptoms (as measured by GSRS, IBS-SSS, BSFS and QoL scales etc.) are reassessed. Trial supplementation products are collected to check compliance. Faecal samples and blood samples are collected and analysed as before.

The treatment patients report a reduction in pain/visceral sensitivity, a reduction in bowel movement frequency and an improvement in stool consistency as compared to the placebo group. The blood biomarker analysis indicates that the treatment patients have reduced levels of inflammatory markers, reduced gut permeability indicating an improved mucosal barrier, and reduced evidence of mast cell degranulation. The faecal analysis indicates that the treatment patients have reduced levels of intestinal dysbiosis and a higher level of bifidobacteria; especially those of the *Bifidobacterium adolescentis* phylogenetic group.

Example 2—Human Trial in Lactose Intolerant Patients

A total of 60 male and female with lactose intolerance are recruited to participate in a randomized double-blind, parallel, placebo-controlled study. After a screening visit and run-in period of 1-2 weeks eligible subjects are randomized into two groups, each of 30 participants. One group is administered a placebo product containing 2 grams of glucose, the other group is administered a treatment product containing 5 grams of a 4:1 mass ratio mix of 2'-FL and LNnT for 30 days.

Inclusion criteria includes adults in the age of 18 to 60 years with current or recent self-reported history of dairy intolerance of at least 1-month duration, and with gastrointestinal symptoms after dairy consumption. Exclusion criteria includes participation in a clinical study one month prior to the screening visit; abnormal results in the screening tests which are clinically relevant for study participation; suffering from a severe disease such as malignancy, diabetes, severe coronary disease, kidney disease, neurological disease, or severe psychiatric disease or any condition which can confound the results of the study; ingested anti-, pre- or probiotics 3 month prior to the study; consumed on a regular basis any medication that might interfere with symptom evaluation 2 weeks prior to the study; and pregnant or lactating.

At the screening visit (first visit), medical history and concomitant medication is registered and blood samples for safety analyses are collected. Lactose intolerance is confirmed by a 25-gram lactose challenge, where gastrointestinal symptoms (associated with lactose intolerance) and hydrogen production are assessed via hydrogen breath test (HBT) for 6 hours post-lactose challenge. A positive HBT is defined as a hydrogen gas elevation of 20 parts per million (ppm) at 4 time-points within 6 hours following a lactose-loading dose. A faecal sample kit is distributed, and participants are instructed to keep their collected faecal samples in the freezer until the next visit.

At the second visit, eligibility criteria are checked and eligible subjects are randomised to the two arms in the trial (treatment and placebo group). Faecal samples are collected and stored at −80° C. until analysis. Equipment for new faecal samples are distributed. Participants are familiarised with an interactive internet enabled system which records data daily and they are provided with either treatment or placebo products. Subjects are asked not to change their usual diet and to avoid dairy products during the 30-day treatment period.

During the 30-day treatment period the participants consume either a placebo or a treatment product daily. Participants are instructed to consume the products in the morning with breakfast. Compliance is monitored through the interactive internet enabled system. The participants also use the system to record:

Bristol Stool Form Scale (BSFS) information.
Gastrointestinal Symptom Rating Scale (GSRS) information.
The GSRS questionnaire includes 15 items covering five dimensions (abdominal pain, indigestion, reflux, diarrhoea, constipation) and uses a seven-graded Likert scale.

At the third visit, after the 30-day treatment period, faecal samples are collected. Additionally, the participants are challenged with 25-gram lactose where lactose digestion are measured by hydrogen production in the HBT and evaluation of gastrointestinal symptoms (associated with lactose intolerance) is measured by participant's self-assessment of symptoms over the 6 hours following the lactose challenge.

After completion of the treatment period, participants are followed for an additional 30 days and instructed to reintroduce dairy foods into their diets. During the follow-up period, participants record BSFS and GSRS information.

At the end of the study, each participant has an exit visit with the medical team and faecal samples are collected.

Lactose digestion is measured by breath hydrogen (BH) production. BH is measured in parts per million (ppm) using a validated hand-held hydrogen chemical sensor (EC60 gastrolyzer, Bedfont Scientific Ltd, United Kingdom). Following a baseline measurement (0 hour), participants ingest 25 g of lactose mixed in water. BH is then remeasured at 30 and 60 min, and at 3 hours and 6 hours after lactose challenge. The baseline value is subtracted from readings recorded at each subsequent time interval. In general, an acceptable baseline value is 20 ppm or lower. A definite positive value is defined as more than 20 ppm above baseline at any time point. Results of each BH measurement are summed to obtain a value for total BH.

Symptoms of lactose intolerance are recorded on a four-point Likert scale at baseline (0 h) and at 3 and 6 hours following the ingestion of 25 g of lactose. Bloating, flatulence, abdominal pain and cramps are assigned using a score of 0 if there were no symptoms, 1 for mild symptoms, 2 for moderate symptoms and 3 for severe symptoms.

To assess the microbiota profile, DNA is extracted from faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 with Illumina adapters attached. These are universal bacterial 16S rDNA primers, which target the V3-V4 region. Following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel. Products from the nested PCR are normalized using the SequalPrep Normalization Plate Kit and pooled. Pooled libraries are concentrated by evaporation and the DNA concentration of pooled libraries is measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH is used for bioinformatical analysis of the sequence data.

Bacterial beta-galactosidase is assessed as measures of stool enzyme activity. Faecal beta-galactosidase is measured by adding 20 µl of faeces homogenised in buffer to 480 µg of O-nitrophenyl-beta-D-galactopyranoside in sodium phosphate buffer (pH 7.0). The reaction is allowed to proceed at 45° C. for 10 min. Sodium carbonate (1 M) is added to stop the reaction. Optical density at 420 nm is subsequently read and beta-galactosidase activity is reported as units/g of stool.

The results show that oral ingestion of HMOs reduce bowel movement frequency and improve stool consistency. The HMOs also modulate the intestinal microbiota, and specifically stimulate the growth of bifidobacteria. The increase in abundance of bifidobacteria occurs at the expense of *Escherichia* and *Clostridium*, which are reduced. The level of bifidobacteria correlated positively with beta-galactosidase, and negatively with hydrogen gas production. Additionally, the results show that symptoms of abdominal pain, cramping, bloating, and flatulence normally provoked by lactose consumption are improved after HMO supplementation in individuals with lactose intolerance. Collectively, HMOs are able to increase bifidobacteria and change the intestinal environment, and by this, reduce gastrointestinal symptoms and in particular diarrhoea.

Example 3—Human Trial in Antibiotic Treated Children

A total of 40 children of age 5 to 10 years are recruited to participate in the study. The children are commencing a broad spectrum, antibiotic therapy prescribed by a doctor for an infectious disorder. All recruited children and their caretakers are able and willing to understand and comply with the study procedures. Children are excluded if: they have participated in a clinical study one month prior to screening visit; they are suffering from a severe disease such as gastro-intestinal diseases, malignancy, diabetes, severe coronary disease, kidney disease, neurological disease, or severe psychiatric disease or any condition which can confound the results of the study; used highly dosed probiotic supplements (yoghurt allowed) for 3 months prior to the study; consumed antibiotic drugs 3 months prior to the study, and consumed on a regular basis any medication that might interfere with symptom evaluation 2 weeks prior to the study.

At a screening visit, medical history and concomitant medication is registered. Additionally, eligibility criteria are checked and eligible subjects are randomised into two groups, each of 20 children. The treatment period (6 weeks) is divided into two, as follows:

Period 1 (2 weeks): Group 1 (placebo), Group 2 (treatment product).

Period 2 (4 weeks): Group 1 (placebo), Group 2 (treatment product).

The treatment product contains 5 grams of a combination of 2'-FL and LNnT (4:1 mass ratio), while the placebo product contains 5 grams of glucose. Both products are in powder form in a sachet. The products are each administered daily as a bolus at breakfast, and diet is not controlled; however, the participants are asked not to change their normal diet over the course of the study.

At the initial visit, faecal sample kits and either treatment or placebo products are distributed. Each child's caretaker is instructed to keep the faecal samples in the freezer until the next visit. The children and caretaker are reminded not to change the children's usual diet during the study. A faecal sample is collected at this visit and stored at −80° C. until analysis.

The study runs for two plus four weeks with the children consuming either placebo and/or treatment product daily. Compliance is monitored through the interactive internet enabled system.

The participants also use the system to record:
Bristol Stool Form Scale (BSFS) information
Questionnaire for Paediatric Functional GI Disorders (QPFG)

The QPFG questionnaire covers dimensions such as abdominal pain and discomfort, bowel movement, and other gastrointestinal symptoms.

At the end of period 1, faecal samples are collected and new treatment or placebo products are distributed. At the end of period 2 (exit visit), each children has a visit with the medical team and faecal samples are collected. After 6 months, faecal samples are collected at a follow up visit.

To assess the microbiota profile, DNA is extracted from the faecal samples using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-21 (Klindworth et al. *Nucleic Acids Res.* 41, e1 (2013)) with Illumina adapters attached. These are universal bacterial 16S rDNA primers, which target the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1% agarose gel.

Products from the nested PCR are normalized using the SequalPrep Normalization Plate Kit and pooled. Pooled libraries are concentrated by evaporation and the DNA concentration of pooled libraries was measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, 2013) is used for bioinformatical analysis of the sequence data.

The faecal analyses reveal that HMOs are able to prevent antibiotic mitigated dysbiosis and enhance a favourable microbiota composition by increasing the abundance of bifidobacteria and especially the *Bifidobacterium adolescentis* phytogenic group during and post antibiotic therapy. Further the children have reduced incidence of diarrhoea.

Example 4—Nutritional Composition

A ready to feed nutritional composition is prepared from water, maltodextrin, corn syrup, sugar, milk protein concentrate, vegetable oil (canola, high oleic sunflower and corn), soy protein isolate, acacia gum, flavours, HMSs/HMOs, potassium citrate, magnesium phosphate, cellulose gel and gum, calcium carbonate, sodium ascorbate, soy lecithin, choline bitartrate, calcium phosphate, alpha-tocopheryl acetate, ascorbic acid, carrageenan gum, ferric pyrophosphate, flavours, sweeteners (Stevia), vitamin A palmitate, niacinamide, vitamin D3, calcium pantothenate, manganese sulphate, copper sulphate, pyridoxine hydrochloride, thiamine hydrochloride, beta carotene, riboflavin, chromium chloride, folic acid, biotin, potassium iodide, phytonadione, sodium selenite, sodium molybdate, vitamin B12.

The composition provides a nutritional supplement which is a good source of protein, low in fat, vitamins, minerals and antioxidants, and meets FODMAP criteria. Further, the composition contains HMSs and/or HMOs which are able to promote the growth of beneficial intestinal bacteria and modulate chronic inflammation.

Example 5—Capsule Composition

A capsule is prepared by filling about 1 g of HMO into a 000 gelatine capsule using a filing machine. The capsules are then closed. The HMO are in free flowing, powder form.

Example 6—Mucosal Barrier Function

2'-FL and LNnT are tested with respect to their ability to induce MUC2, TFF3, EIMβ, CHST5, and GAL3ST2 expression in the human LS174T cell culture model of goblet cells. The human LS174T cell line is obtained from the American Type Culture Collection (ATCC). LS174T cells are maintained in minimum essential medium (MEM) supplemented according to instructions at 37° C. in 5% $CO_2$. 2'-FL and LNnT are dissolved in cell culture grade water to the required concentration. The LS174T cells are treated with the HMO solution containing 0 or 5 mg HMO/ml.

The LS174T cells are collected and suspended in Trizol reagent and total RNA is isolated using an RNA analysis kit (Qiagen) according to the manufacturer's instructions and the RNA isolates are quantified using Nanodrop analysis (Thermo Fisher Scientific). RNA isolates are reverse transcribed using a high capacity cDNA Reverse Transcription Kit (Applied Biosystems) to create cDNA, which is then used to assess gene expression via quantitative RT-PCR.

For the quantitative RT-PCR, specific TaqMAN gene expression assays are obtained from Applied Biosystems, which include expression assays for MUC2, TFF3, CHST5 and GAL3ST2. Quantitative real-time PCR is performed using TaqMAN PCR Master Mix (Applied Biosystems). Reactions are run in duplicates in a 384-well plate using an Applied Biosystems 7900HT Fast Real-Time PCR System. The results are analysed using SDS 2.3 software and calculated by delta delta Ct method. All samples are normalized to Gus-β expression and fold induction is calculated over untreated controls. Gene expression is expressed as fold increase compared to HMO-free control cells. The experiment is repeated three times.

The results indicate that treatment with 2'-FL and LNnT increases the expression of the MUC2 and TFF3 genes compared to control cultures. Increased expression of goblet cell genes is specific and not universal, as evidenced by the minimal induction or lack of induction of CHST5 and GAL3 ST2, respectively. MUC2 and TFF3 are key components of the mucosal barrier and improve mucosal barrier function.

What is claimed is:

1. A method comprising:
   selecting a non-infant human experiencing one or more symptoms associated with diarrhea-predominant irritable bowel syndrome ("IBS-D");
   selecting an effective amount of a mixture of the human milk oligosaccharides ("HMOs") 2'-fucosyllactose (2'FL) and lacto-N-neotetraose (LNnT) for administration to the non-infant human that when administered to the non-infant human reduces a level of intestinal dysbiosis by increasing the relative abundance of Bifidobacterium adolescentis; and
   increasing the relative abundance of Bifidobacterium adolescentis in the gastrointestinal microbiota of the non-infant human and reducing the one or more symptoms associated with the IBS-D in the non-infant human by administering to the non-infant a daily dose of the selected effective amount of the mixture of 2'FL and LNnT.

2. The method of claim 1, further comprising improving an impaired mucosal barrier in the non-infant human by administering to the non-infant human the selected effective amount of the mixture of 2'FL and LNnT.

3. The method of claim 1, wherein reducing the one or more symptoms associated with IBS-D comprises reducing bowel movement frequency and improving stool consistency.

4. The method of claim 1, further comprising reducing levels of an inflammatory marker in the non-infant human by administering to the non-infant human the selected effective amount of the mixture of 2'FL and LNnT.

5. The method of claim 1, further comprising administering with the mixture of 2'FL and LNnT, one or more additional HMOs selected from the group consisting of 3-fucosyllactose (3FL), difucosyllactose (DFL), lacto-N-tetrose (LNT), 3'-sialyllactose (3'SL), 6'-sialyllactose (6'SL), lacto-N-fucopentaose I (LNFP-I), and combinations thereof.

6. The method of claim 1, wherein the mass ratio of the 2'FL to the LNnT is from about 4:1 to 2:1.

7. The method of claim 1, wherein the selected effective amount of the administered mixture of 2'FL and LNnT is from about 3 g to about 7.5 g per day.

8. The method of claim 1, further comprising reducing levels of Escherichia and Clostridium in the non-infant human.

9. A method comprising:
   selecting a non-infant human experiencing lactose intolerance and one or more symptoms associated with the lactose intolerance, the symptoms selected from diarrhea, abdominal pain, cramping, bloating, and flatulence;
   selecting an amount of a mixture of the human milk oligosaccharides ("HMOs") 2'-fucosyllactose (2'FL) and lacto-N-neotetraose (LNnT) effective for increasing the relative abundance of Bifidobacterium adolescentis in the gastrointestinal microbiota of the non-infant human; and
   increasing the relative abundance of Bifidobacterium adolescentis in the gastrointestinal microbiota of the non-infant human and reducing at least one of the one or more gastrointestinal symptoms of the lactose intolerance by administering to the non-infant human a daily dose of the selected effective amount of the mixture of 2'FL and LNnT.

10. The method of claim 9, wherein:
    after an initial treatment period, the non-infant human reintroduces consumption of dairy foods; and administering the mixture reduces the likelihood of the symptoms of lactose intolerance occurring in the non-infant human after the initial treatment period.

11. A method comprising:
    selecting a non-infant human commencing an antibiotic therapy;
    selecting an amount of a mixture of the human milk oligosaccharides ("HMOs") 2'-fucosyllactose (2'FL) and lacto-N-neotetraose (LNnT) effective for increasing the relative abundance of Bifidobacterium adolescentis in the gastrointestinal microbiota of the non-infant human; and
    increasing the relative abundance of Bifidobacterium adolescentis in the gastrointestinal microbiota of the non-infant human and reducing the likelihood of the non-infant human experiencing gastrointestinal dysbiosis, diarrhea, or both, associated with the antibiotic therapy by administering to the non-infant human a daily dose of the selected effective amount of the mixture of 2'FL and LNnT.

12. The method of claim 11, further comprising reducing levels of Clostridium in the non-infant human.

13. The method of claim 12, further comprising reducing the likelihood of the non-infant human experiencing diarrhea associated with the Clostridium during the antibiotic therapy.

14. The method of claim 12, further comprising reducing the likelihood of the non-infant human experiencing diarrhea associated with the Clostridium during a post antibiotic therapy period of up to four weeks.

15. The method of claim 9, further comprising reducing hydrogen gas production in the gastrointestinal tract of the non-infant human.

16. The method of claim 9, further comprising increasing the beta-galactosidase activity in the gastrointestinal tract of the non-infant human.

* * * * *